US012733635B2

(12) United States Patent
Zheng et al.

(10) Patent No.: US 12,733,635 B2
(45) Date of Patent: Sep. 15, 2026

(54) PLATELET STORAGE METHODS AND COMPOSITIONS

(71) Applicant: Platefuse, Inc., Cincinnati, OH (US)

(72) Inventors: Yi Zheng, Cincinnati, OH (US); Jose Cancelas, Cincinnati, OH (US)

(73) Assignee: Platefuse, Inc., Cincinnati, OH (US)

( * ) Notice: Subject to any disclaimer, the term of this patent is extended or adjusted under 35 U.S.C. 154(b) by 953 days.

(21) Appl. No.: 17/792,890

(22) PCT Filed: Jan. 13, 2021

(86) PCT No.: PCT/US2021/013311
§ 371 (c)(1),
(2) Date: Jul. 14, 2022

(87) PCT Pub. No.: WO2021/146341
PCT Pub. Date: Jul. 22, 2021

(65) Prior Publication Data

US 2023/0086683 A1 Mar. 23, 2023

Related U.S. Application Data

(60) Provisional application No. 62/961,580, filed on Jan. 15, 2020.

(51) Int. Cl.
*C07D 215/42* (2006.01)
*A01N 1/125* (2025.01)
*A01N 1/162* (2025.01)
*A61K 35/19* (2015.01)
*C07D 401/12* (2006.01)
*C12N 5/078* (2010.01)

(52) U.S. Cl.
CPC ............. *A01N 1/125* (2025.01); *A01N 1/162* (2025.01); *A61K 35/19* (2013.01); *C07D 215/42* (2013.01); *C07D 401/12* (2013.01); *C12N 5/0644* (2013.01)

(58) Field of Classification Search
CPC ............................ C07D 215/42; C07D 401/12
See application file for complete search history.

(56) References Cited

U.S. PATENT DOCUMENTS 4,994,367 A 2/1991 Bode et al.
5,141,851 A 8/1992 Brown et al.
5,238,922 A 8/1993 Graham et al.
5,420,245 A 5/1995 Brown et al.
5,420,334 A 5/1995 Singh et al.
5,436,128 A 7/1995 Harpold et al.
5,447,922 A 9/1995 Lawrence et al.
5,470,832 A 11/1995 Gibbs et al.
5,482,954 A 1/1996 Kohn et al.
5,510,510 A 4/1996 Patel et al.
5,523,430 A 6/1996 Patel et al.
5,567,841 A 10/1996 Magnin et al.
5,574,025 A 11/1996 Anthony et al.
5,602,098 A 2/1997 Sebti et al.
5,618,964 A 4/1997 Cheng et al.
5,629,302 A 5/1997 Eugster et al.
5,631,401 A 5/1997 Stein et al.
5,705,686 A 1/1998 Sebti et al.
5,756,528 A 5/1998 Anthony et al.
5,773,455 A 6/1998 Dong et al.
5,786,193 A 7/1998 Greene et al.
5,817,678 A 10/1998 Kim et al.
5,830,868 A 11/1998 Bolton et al.
5,834,434 A 11/1998 Sebti et al.
5,843,941 A 12/1998 Marsters, Jr. et al.
5,928,924 A 7/1999 Greene et al.
5,929,077 A 7/1999 Leftheris
6,011,029 A 1/2000 Ding et al.
6,083,979 A 7/2000 Sebti et al.
6,156,746 A 12/2000 Leftheris et al.
6,166,067 A 12/2000 Kriimer et al.
6,191,147 B1 2/2001 Brown et al.

(Continued)

FOREIGN PATENT DOCUMENTS

EP 2014651 1/2009
EP 3310761 4/2018

(Continued)

OTHER PUBLICATIONS

European Search Report regarding Application No. 27140874.9-1110/4090657 PCT/US2021013311, dated Nov. 20, 2023 for Applicant Platefuse, Inc., pp. 1-8.

(Continued)

*Primary Examiner* — Brian E McDowell

(74) *Attorney, Agent, or Firm* — Tarolli, Sundheim, Covell & Tummino LLP

(57) ABSTRACT

Disclosed are compounds according to formula I:

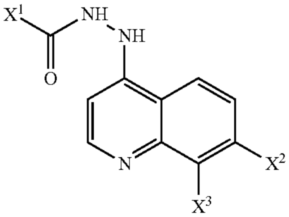

and compositions for slowing, preventing, or reversing platelet damage, particularly as may occur during blood banking or during refrigeration of platelets. Also disclosed herein are methods for storing platelets and methods of improving platelet survival upon transfusion with one or more compounds or compositions as described herein.

8 Claims, No Drawings

(56) References Cited

U.S. PATENT DOCUMENTS

| | | | |
|---|---|---|---|
| 6,194,438 | B1 | 2/2001 | Yang et al. |
| 6,197,771 | B1 | 3/2001 | Bigge et al. |
| 6,211,193 | B1 | 4/2001 | Remiszewski et al. |
| 6,214,827 | B1 | 4/2001 | Afonso et al. |
| 6,214,828 | B1 | 4/2001 | Doll et al. |
| 6,218,401 | B1 | 4/2001 | Afonso et al. |
| 6,225,322 | B1 | 5/2001 | Cooper et al. |
| 6,228,856 | B1 | 5/2001 | Njoroge et al. |
| 6,228,865 | B1 | 5/2001 | Doll et al. |
| 6,239,140 | B1 | 5/2001 | Cooper et al. |
| 6,242,433 | B1 | 6/2001 | Balsamo et al. |
| 6,242,458 | B1 | 6/2001 | Bishop et al. |
| 6,248,756 | B1 | 6/2001 | Anthony et al. |
| 6,258,824 | B1 | 7/2001 | Yang |
| 6,262,110 | B1 | 7/2001 | Shaikenov et al. |
| 6,265,382 | B1 | 7/2001 | Doherty et al. |
| 6,268,394 | B1 | 7/2001 | Shaikenov et al. |
| 6,277,854 | B1 | 8/2001 | Njoroge et al. |
| 6,294,552 | B1 | 9/2001 | Lyssikatos et al. |
| 6,316,462 | B1 | 11/2001 | Bishop et al. |
| 6,329,376 | B1 | 12/2001 | Bergman |
| 6,358,968 | B1 | 3/2002 | Remiszewski et al. |
| 6,362,188 | B1 | 3/2002 | Guzi et al. |
| 6,372,747 | B1 | 4/2002 | Taveras et al. |
| 6,376,496 | B1 | 4/2002 | Hartman et al. |
| 6,387,903 | B1 | 5/2002 | Dinsmore et al. |
| 6,387,905 | B2 | 5/2002 | Njoroje et al. |
| 6,387,926 | B1 | 5/2002 | Bhide et al. |
| 6,387,948 | B1 | 5/2002 | Kwon et al. |
| 6,399,615 | B1 | 6/2002 | Guzi et al. |
| 6,403,581 | B1 | 6/2002 | Ayral-Kaloustain et al. |
| 6,410,541 | B2 | 6/2002 | Remiszewski et al. |
| 6,423,751 | B1 | 7/2002 | Liao |
| 6,426,352 | B1 | 7/2002 | Njoroge et al. |
| 6,432,959 | B1 | 8/2002 | Cooper et al. |
| 6,440,974 | B2 | 8/2002 | Doll et al. |
| 6,440,989 | B2 | 8/2002 | Afonso et al. |
| 6,441,017 | B1 | 8/2002 | Bell et al. |
| 6,451,812 | B1 | 9/2002 | End et al. |
| 6,458,783 | B1 | 10/2002 | Ding et al. |
| 6,458,935 | B1 | 10/2002 | Burns et al. |
| 6,492,381 | B1 | 12/2002 | Bishop et al. |
| 6,495,564 | B1 | 12/2002 | Lyssikatos et al. |
| 6,500,841 | B1 | 12/2002 | Desolms et al. |
| 6,511,800 | B1 | 1/2003 | Singh |
| 6,528,523 | B2 | 3/2003 | Njoroge et al. |
| 6,535,820 | B1 | 3/2003 | Stickland et al. |
| 6,539,309 | B1 | 3/2003 | Stickland et al. |
| 6,545,020 | B1 | 4/2003 | Van Ginckel et al. |
| 6,572,850 | B1 | 6/2003 | Mandeville, III et al. |
| 6,576,639 | B1 | 6/2003 | Doll et al. |
| 6,579,887 | B2 | 6/2003 | Lyssikatos et al. |
| 6,586,447 | B1 | 7/2003 | Lyssikatos et al. |
| 6,586,461 | B1 | 7/2003 | Gibbs |
| 6,596,735 | B1 | 7/2003 | Yang |
| 6,615,359 | B2 | 9/2003 | Eyres et al. |
| 6,617,359 | B2 | 9/2003 | Wohlfart et al. |
| 6,649,638 | B1 | 11/2003 | Brown et al. |
| 7,122,570 | B2 | 10/2006 | Koppitz et al. |
| 7,417,026 | B2 | 8/2008 | Williams et al. |
| 7,517,890 | B2 | 4/2009 | Zheng et al. |
| 7,612,080 | B2 | 11/2009 | Zheng et al. |
| 7,826,982 | B2 | 11/2010 | Zheng et al. |
| 8,383,124 | B2 | 2/2013 | Zheng et al. |
| 10,028,503 | B2 | 7/2018 | Zheng et al. |
| 10,405,538 | B2 | 9/2019 | Zheng et al. |
| 11,172,673 | B2 | 11/2021 | Zheng et al. |
| 2004/0137518 | A1 | 7/2004 | Lambert et al. |
| 2005/0049294 | A1 | 3/2005 | Palladino et al. |
| 2005/0069553 | A1 | 3/2005 | Zheng et al. |
| 2005/0238666 | A1 | 10/2005 | Williams et al. |
| 2006/0135542 | A1 | 6/2006 | Zheng et al. |
| 2009/0041737 | A1 | 2/2009 | Maurer et al. |
| 2013/0202553 | A1 | 8/2013 | Zheng |
| 2022/0061312 | A1 | 3/2022 | Zheng et al. |

FOREIGN PATENT DOCUMENTS

| | | |
|---|---|---|
| GB | 1424359 | 2/1976 |
| WO | WO 04/076445 | 9/2004 |
| WO | WO 05/017160 | 2/2005 |
| WO | WO 05/037791 | 4/2005 |
| WO | WO 05/051392 | 6/2005 |
| WO | WO 06/055833 | 5/2006 |
| WO | 2006064237 A2 | 9/2006 |
| WO | 2006064237 A3 | 9/2006 |
| WO | WO 09/114725 | 9/2009 |
| WO | WO 13/166043 | 11/2013 |
| WO | WO 14/120683 | 8/2014 |
| WO | 2016204809 A1 | 12/2016 |
| WO | WO 16/204809 | 12/2016 |

OTHER PUBLICATIONS

New 5-Hydroxy-2-indolecarbohydrazides as Platelet Aggregation Inhibitors in Ethylene Glycol, A. Monge, et al., date, Journal of Pharmaceutical Sciences, pp. 1025-1027.
Akbar et al., Dec. 6, 2014, RhoA and Rac1 Gtpases Differentially Regulate Agonist-Receptor Mediated ROS Generation in Platelets, Blood, 124(21 ), Abstract Only, 2 pgs.
Akbar et al., 2004, Rac2 GTPase plays a critical role in platelet adhesion as well as in sustenance and perpetuation of platelet aggregation, Blood, 104:Abstract 3523.
Akbar et al., 2006, [43] Rational Design and Application of a RAC GTPase-Specific Small Molecule Inhibitor Regulations and Effectors of Small GTPases: RHO Family; Methods in Enzymology, 406:554-565.
Akbar et al., 2007, Genetic and pharmacologic evidence that Rac1 GTPase is involved in regulation of platelet secretion and aggregation, Journal of Thrombosis and Haemostasis, 5:1747-1755.
Akbar et al., 2015, Abstract 58: Differential Signaling by CRP-PACI-NOXI and Thrombin-Pac I-NOX2 Axes Regulates Ros Generation and Platelet Activation, Arteriosclerosis, Thrombosis, and Vasular Biology, 35:A58.
Akbar et al., Jul. 2011, Gene Targeting Implicates Cdc42 GTPase in GPVI and Non-GPVI Mediated Platelet Filopodia Formation, Secretion and Aggregation, PLoS ONE, 6(7):e22117, 9 pp.
Akbar et al., Sep. 28, 2016, RhoA and Rac1 GTPases differentially regulate agonist-receptor mediated reactive oxygen species generation in platelets, PLoS One, 11(9):e0163227.doi:10.1371/journal.pone.0163227.
Antinarelli et al., 2015, 4-aminoquinoline derivatives as potential antileishmanial agents, Chemical biology & drug design, 86(4):704-714.
Arikawa et al., Aug. 29, 2003, Ligand-dependant inhibition of B16 melanoma cell migration and invasion via endogenous S1P2 G protein-coupled receptor. Requirement of inhibition of cellular RAC activity, J Biol Chem, 278(35):23841-51.
Aslan et al., 2012, Rho GTPases in platelet function, Journal of Thrombosis and Haemostasis, 11:35-46.
Aubuchon et al., Jul. 2005, Comparison of computerized formulae for determination of platelet recovery and survival, Letter to the Editor, Transfusion, 45:1237-1238.
Bastola et al., 2002, Downregulation of PTEN/MMAC/TEP1 expression in human prostate cancer cell line DU145 by growth stilului, Mol. Cell Biochem., 236:75-81.
Behnke, 1970, Effects of Some Chemicals on Blood Platelet Microtubules, Platelet Shape and Some Platelet Functions in vitro, Scand. J. Haemat., 7:123-140.
Blann et al., 1997, Evidence of platelet activation in hypertension, J Hum Hypertens, 11:607-609.
Broijersen et al., 2001, Platelet activity In Vivo in hyperlipoproteinemia—Importance of combined hyperlipidemia, Thromb Haemost, 79:268-275.
Cancelas et al., Aug. 2005, Rac GTPases differentially integrate signals regulating hemotopoietic stem cell localization, Nature Medicine, 11(8):886-891.
Cancelas, Jun. 19, 2018, Future of platelet formulations and storage, RDCR Symposium Thor group, Bergen, Norway, 40 pp.

(56) References Cited

OTHER PUBLICATIONS

Chemical Abstract compound, STNext. RN 92856-78-5(Entered STN: Dec. 17, 1984), 1 p.
Chemical Abstract compounds, STNext. RN 924202-68-6 (Entered STN: Mar. 1, 2007), RN 727980-43-0 (Entered STN: Aug. 18, 2004), 1 p.
Chemical Abstract compounds, STNext. RN 920646-81-7 (Entered STN: Feb. 13, 2007), RN 1814906-80-3 (Entered STN: Oct. 26, 2015), RN 1448458-25-0 (Entered STN: Aug. 15, 2013), RN 949563-10-4 (Entered STN: Oct. 7, 2007), RN 949563-09-1 (Entered STN: Oct. 7, 2007), RN 930729-10-5 (Entered STN: Apr. 18, 2007), 3 pp.
Chuang et al., Oct. 1995, Abr and Bcr are multifunctional regulators of the Rho GTP-binding protein family, Proc. Natl. Acad. Sci. USA, Biochemistry, 92:10202-10286.
Clark et al., 2002, Consensus scoring for ligand/protein interactions, J Mol Graph Model, 20:281-295.
De Jong et al., 1995, Tyrosine phosphorylation of murine Crkl, Oncogene, 11:1469-1474.
De Jong et al., Sep. 15, 1995, Crkl is Complexed with Tyrosine-phosphorylated Cbl in Ph-positive Leukemia, The Journal of Biological Chemistry, 270(37):21468-21471.
Deininger et al., Nov. 15, 2000, The molecular biology of chronic myeloid leukemia, Blood, 96(10):3343-3356.
Del Pozo et al., 2000, Adhesion to the extracellular matrix regulates the coupling of the small GTPase Rac to its effector PAK, EMBO J., 19:2008-2014.
Delaney et al., Nov. 2012, The Role of Rac1 in Glycoprotein Ib-IX-Mediated Signal Transduction and Integrin Activation, Arerioscler Thromb Vasc Biol, 32:2761-2768.
Dumont et al., Jan. 2013, A randomized controlled trial evaluating recovery and survival of 6% dimethly sulfozide-frozen autologous platelets in healthy volunteers, Transfusion, 53:128-137.
Dumont et al., May 2013, Invitro and in vivo quality of leukoreduced apheresis platelets stored in a new platelet additive solution, Transfusion, 53:972-980.
Dunbrack et al., 1997, Bayesian statistical analysis of protein side-chain rotamer preferences, Protein Science, 6:1661-1681.
Eder et al., Jul. 2007, Bacterial screening of apheresis platelets and the residual risk of septic transfusion reactions: the American Red Cross experience (2004-2006) , Transfusion, 47:1134-1142.
Engers et al., 2000, Tiaml mutations in human renal-cell carcinomas, Int J Cancer, 88:369-376.
Etienne-Manneville et al., Dec. 2002, Rho GTPases in Cell Biology, Nature, 420:629-635.
Falet et al., Nov. 19, 2009 Platelet-associated IgAs and impaired GPVI responses in platelets lacking WIP, Blood, 114(21):4729-4737.
Fiegen et al., Feb. 6, 2005, Alternative splicing of Rac1 generates Rac1b, a Self-activating GTPase, J Biol Chem, 29(6):4743-4749.
Fioretos et al., 1995, Regional Localization and Developmental Expression of the BCR Gene in Rodent Brain, Cell Mol Biol Res., 41(2):97-102.
Fioretos et al., 1995, Standpoint on imprinting of BCR and ABL, Leukemia, 9(4):743-44.
Fitzgerald et al., 1996, Platelet activation in unstable coronary disease, N Engl J Med., 315:983-989.
Florian et al., May 4, 2012, CDC42 Activity Regulates Hematopoietic Stem Cell Aging and Rejuvenation, Cell Stem Cell., 10(5):520-530.
Flower et al., 2002, Drug design, cutting edge approaches, Royal Society of Chemistry, Cambridge, UK, pp. 21-27.
Flyvbjerg et al., 1995, Stimulation of hepatic insulin-like growth factor-binding protein-1 and -3 gene expression by octreotide in rats, Journal of Endrocrinology, 147:545-551.
Fontaine et al., Oct. 2009, Improving platelet supply chains through collaborations between blood centers and transfusion services, Transfusion, 49:2040-2047.
Fritz et al., 1999, Rho GTPases are over-expressed in human tumors, Int J Cancer, 81:682-687.
Fuller et al., Dec. 2009, Bacterial culture reduces but does not eliminate the risk of septic transfusion reactions to single-donor platelets, Transfusion, 49:2588-2593.
Gao et al., 2001, $Trp^{56}$ of Rac1 Specifies Interaction with a Subset of Guanine Nucleotide Exchange Factors, J Biol Chem, 276:47530-47541.
Gao et al., May 18, 2004, Rational design and characterization of a RAC GTPase-specific small molecule inhibitor, PNAS, 101(20):7618-7623.
Gawaz, 2004, Role of platelets in coronary thrombosis and reperfusion of ischemic myocardium, Cardiovas. Res.61:498-511.
Goodford, 1985, A Computational Procedure for Determining Energetically Favorable Binding Sites on Biologically Important Macromolecules, J Med Chem, 28:849-857.
Grizot et al., 2001, Crystal Structure of the Rac1-RhoGDI Complex Involved in NADPH Oxidase Activation, Biochemistry, 40:10007-10013.
Groffen, 1995, Two candidate breast cancer genes on chromosome, Childrens Hospital, Los Angeles, Research Project Awards abstract, 1 p.
Gruneberg et al., 2001, Subnanomolar Inhibitors from Computer Screening: A Model Study Using Human Carbonic Anhydrase II, Chem Int Ed Engl., 40:389-393.
Gu et al., 2003, Hematopoietic Cell Regulation by Rac1 and Rac2 Guanosine Triphosphatases, Science, 302:445-449.
Guo et al., 2003, $p19^{Arf}$-p53 Tumor Suppressor Pathway Regulates Cell Motility by Suppression of Phosphoinositide 3-Kinase and Rac1 GTPase Activities, J Biol Chem, 278(16):14414-14419.
Guyatt et al., 2001, Grades of Recommendation for Antithrombotic Agents, Chest, 119:38-7S.
Haataja et al., Aug. 15, 1997, Characterization of Rac3, a Novel Member of the Pho Family, The Journal of Biological Chemistry, 272(33):20384-20388.
Haataja et al., Jan. 1, 1997, Deletion within the D17S34 Locus in a Primitive Neuroectodermal Tumor, Cancer Research, 57:32-34.
Hartwig, Sep. 1992, Mechanisms of Actin Rearrangements Mediating Platelet Activation, The Journal of Cell Biology, 118(6):1421-1442.
Haszon et al., 2003, Platelet aggregation, blood viscosity and serum lipids in hypertensive and obese children, Eur J Pediatr, 162:385-390.
Hawkins et al., 1995, PDGF stimulates an increase in GTP-Rac via activation of phosphoinostitide 3-kinase, Curr Biol, 5:393-403.
Heeschen et al., 2003, Soluble CD40 Ligand in Acute Coronary Syndromes, N Engl J Med, 348:1104-1111.
Heisterkamp et al., 1995, Localization of the Human Mitochondrial Citrate Transporter Protein Gene to Chromosome 22Q11 in the DiGeorge Syndrome Critical Region, Geonomics, 29:451-456.
Hoffmeister et al., Jan. 10, 2003, The Clearance Mechanism of Chilled Blood Platelets, Cell, 112:87-97.
Hoffmeister et al., Jan. 25, 2008, Cyclic Nucleotide-dependant Protein Kinases Inhibit Binding of 14-3-3 to the GTPase-activating Protein Rap1GAP2 in Platelets, The Journal of Biological Chemistry, 283(4):2297-2306.
Hoffmeister et al., Jul. 6, 2001, Mechanisms of Cold-induced Platelet Actin Assembly, The Journal of Biological Chemistry, 276(27):24751-24759.
Hoffmeister et al., Sep. 12, 2003, Glycosylation Restores Survival of Chilled Blood Platelets, Science, 301:1531-1534.
Hornsey et al., 2006, Extended storage of platelets in SSP+ platelet additive solution, Vox Sanguinis, 91:41-46.
Huo et al., 2004, Role of Platelets in the Development of Atherosclerosis, Trends Cardiovasc Med, 14:18-22.
Hurst, 1994, Flexible 3D Searching: The Directed Tweak Technique, J Chem Inf Comput Sci, 34:190-196.
Jacobs et al., Dec. 2011, Detection of bacterial contamination in prestorage culture-negative apheresis platelets on day of issue with the Pan Genera Detection test, Transfusion, 51:2573-2582.
Kaartinen et al., Dec. 1995, Abnormal lung development and cleft palate in mice lacking TGF-B3 indicates defects of epithelial-mesenchymal interaction, Nature Genetics, 11:415-421.

(56) References Cited

OTHER PUBLICATIONS

Kaempchen et al., 2003, Upregulation of the Rac1/JNK signaling pathway in primary human schwannoma cells,Hum Mol Genet, 12(11):1211-1221.
Kaighn et al., 1979, Establishment and characterization of human prostatic carcinoma cell line (PC-3), Invest Urol, 17(1):16-23, abstract only.
Kamai et al., 2001, Overexpression of RhoA mRNA is associated with advanced stage in testicular germ cell tumor, BJU Int., 87:227-231.
Karnoub et al., 2001, Molecular basis for Rac1 recognition by guanine nucleotide exchange factors. Nat Struct Biol. 8:1037-1041.
Kato-Stankiewicz et al., 2002, Inhibitors of Ras/Raf-1 interaction identified by two-hybrid screening revert Ras-dependant transformation phenotypes in human cancer cells, PNAS, 99(22):14398-14403.
Kawano et al., 2002, Smooth Muscle Contraction by Small GTPase Rho, Nagoya J. Med.Sci., 65:1-8.
Khosravi-Far et al., Nov. 1995, Activation of Rac1, RhoA, and Mitogen-Activated Protein Kinases Is Required for Ras Transformation, Mol Cell Biol, 15(11):6443-6453.
Lang et al., 2002, Enhanced Expression of Vimentin in Motile Prostate Cell Lines and in Poorly Differentiated and Metastasis Prostate Carcinoma, Prostate, 52:253-263.
Levay et al., Jul. 24, 2013, NSC23766, a Widely Used Inhibitor of Rac1 Activation, Additionally Acts as a Competitive Antagonist at Muscarinic Acetylcholine Receptors, J Pharm and Exp Therap, 347(1):69-79.
Liliental et al., 2000, Genetic deletion of the Pten tumor suppressor gene promotes cell motility by activation of Rac1 and Cdc42 GTPases, Curr Bio, 10:401-404.
Liu et al., 2008, Mobilization of Hematopoitic Stem/Progenitor Cells by a Cdc42 Activity Specific Inhibitor, 2008 ASH Annual Meeting Abstracts, Abstract 68, 112(11):32-33.
Macherla et al., 2005, Structure—Activity Relationship Studies of Salinospotamide A (NPI-0052), a Novel Marine Derived Proteasome Inhibitor, J Med Chem., 48:3684-3687.
Manduteanu et al., 1992, Increased adhesion of human diabetic platelets to cultured valvular endothelial cells, J Submicrosc Cytol Pathol, 24(4):539-547.
Martens et al., 1995, Characterization of Baculovirus Insecticides Expressing Tailored Bacillus thuringiensis CryIA(b) Crystal Proteins, Journal of Invertebrate Pathology, 66:249-257.
Mcdonald et al., 2001, Evaluation of donor arm disinfection techniques, Vox Sanguinis, 80:135-141.
Mcdonald et al., 2002, Evaluation of the 3D BacT/Alert automated system for the detection of microbial contamination of platelet concentrates, Transfusion Medicine, 12:303-309.
Mcdonald et al., 2004, Relative values of the interventions of diversion and improved donor-arm disinfection to reduce the bacterial risk from blood transfusion, Vox Sanguinis, 86:178-182.
Mcdonald et al., 2005, Pall eBDS: an enhanced bacterial detection system for screening platelet concentrates, Transfusion Medicine, 15:259-268.
Mira et al., 2000, Endogenous, hyperactive Rac3 controls proliferation of breast cancer cells by a p21-activated kinase-dependent pathway, PNAS, 97:185-189.
Mononen et al., Mar. 1995, Recombinant glycosylasparaginase and in vitro correction of aspartylglycosaminuria, The FASEB Journal, 9:428-433.
Morris et al., 1995, Spatial organization of ABR and CRK genes on human chromosome band 17p13.3, Oncogene, 10:1009-1011.
Movilla et al., 2001, How Vav proteins discriminate the GTPases Rac1 and RhoA from Cdc42, Oncogene, 20:8057-8065.
Murphy et al., May 15, 1969, Platelet Preservation: Effect of Storage Temperature on Maintenance of Platelet Visibility—Deleterious Effect of Refrigerated Storage, The New England Journal of Medicine, 280(20):1094-1098.
Narumiya, et al., 1993, rho Gene Products, Botulinum C3 Exoenzyme and Cell Adhesion, Cell Signal, 5(1):9-19.
Nassar et al., 2006, Structure-Function Based Design of Small Molecule Inhibitors Targeting Pho Family GTPases, Current Topics in Medicinal Chemistry, 6:1109-1116.
Nityanand et al., 1993, Platelets in Essential Hypertension, Thromb Res, 72:447-454.
Norman, Mar. 13, 2001, Cutting Edge Approaches to Drug Design, IDRUGS, 4(6):659-661.
Nur-E-Kamal et al., 1999, The CDC42-specific inhibitor derived from ACK-1 blocks v-Ha-Ras-induced transformation, Oncogene, 18:7787-7793.
Pelish et al., Jun. 14, 2006, The Cdc42 inhibitor secramine B prevents cAMP-induced K+ conductance in intestinal epithelial cells, Biochemical Pharmacology, 71(12):1720-1726.
Perola et al., 2000, Successful Virtual Screening of a Chemical Database for Farnesyltransferase Inhibitor Leads, J Med Chem, 43:401-408.
Preston et al., 2003, Effects of Severe Hypertension on Endothelial and Platelet Microparticles, Hypertension, 41:211-217.
Qiu et al., Jun. 1997, Cdc42 Regulates Anchorage-Independent Growth and is Necessary for Ras Transformation, Mol Cell Biol, 17(6):3449-3458.
Rarey et al., 1996, A Fast Flexible Docking Method using an Incremental Construction Algorithm, J Mol Biol, 261:470-489.
Ridley et al., 1992, The Small OTP-Binding Protein rac Regulates Growth Factor-Induced Membrane Ruffling, Cell, 70:401-410.
Roberts et al., Feb. 1999, Deficiency of the Hematopoietic Cell-Specific Rho Family GTPase Rac2 Is Characterized by Abnormalities in Neutrophil Function and Host Defense, Immunity, 10:183-196.
Rumjantseva et al., Nov. 2009, Dual roles for hepatic lectin receptors in the clearance of chilled platelets, Nature Medicine, 15(11):1273-1280.
Sahai et al., 2002, Rho-GTPases and Cancer, Nature Reviews Cancer, 2:133-142.
Sahai et al., Aug. 2003, Differing modes of tumor cell invasion have distinct requirements for Rho/Rock signalling and extracellular proteolysis, Nat Cell Biol, 5(8):711-719.
Schmidt et al., 2002, Guanine nucleotide exchange factors for Rho GTPases: turning on the switch, Genes Dev., 16:1587-1609.
Schmitz et al., 2000, Rho GTPases: Signaling, Migration, and Invasion, Exp Cell Res, 261: 1-12.
Schnelzer et al., 2000, Rac1 in human breast cancer: overexpression, mutation analysis, and characterization of a new isoform, Rac1b, Oncogene, 19:3012-3020.
Sekine et al., 1989, Asparagine Residue in the rho Gene Product Is the Modification Site for Botulinum ADP-ribosyltransferase, J Biol Chem., 264:8602-8605.
Serebruany et al., 1999, Increased soluble platelet/endothelial cellular adhesion molecule-1 and osteonectin levels in patients with severe congestive heart failure. Independence of disease etiology, and antecendent aspirin therapy, Eur J Heart Failure, 1:243-249.
Shang et al., 2012, Chapter 3: Rational Design of Rho GTPase-Targeting Inhibitors, Rational Drug Design: Methods and Protocols, Methods in Molecular Biology, 928:29-38.
Shang et al., Jun. 22, 2012, Rational Design of Small Molecule Inhibitors Targeting RhoA subfamily Rho GTPases, Chem Biol, 19(6):699-710.
Silver, May 2004, Genome-Wide Nucleic Acid/Protein Interaction in Breast Cancer, Dana-Farber Cancer Institute, 14 pp.
Skorski et al., 1998, BCR/ABL-mediated leukemogenesis requires the activity of the small GTP-binding protein Rac, PNAS, 95(20):11858-11862.
Sorof et al., 2002, Obesity Hypertension in Children, a Problem of Epidemic Proportions, Hypertension, 40:441-447.
Stepan et al., 1999, Gastrin induces c-fos gene transcription via multiple signaling pathways, Am J Physiol, 276:G415-G424.
Suwa et al., 1998, Overexpression of the rhoC gene correlates with the progression of ductal adenocarcinoma of the pancreas, Br J Cancer, 77:147-152.
Symons, 2000, Adhesion signaling: PAK meets Rac on solid ground, Curr Biol, 10:R535-R537.

(56) References Cited

OTHER PUBLICATIONS

The Royal Childrens Hospital Melbourne, Nov. 3, 2012, Platelet transfusion, https://web.archive.org/web/20121103004450/https://www.rch.org.au/bloodtrans/about_blood_products/Platelet_transfusion/.

The SALT Collaborative Group, Nov. 30, 1991, Swedish Aspirin Low Dose Trial (SALT) of 75 mg aspirin as secondary prophylaxis after cerebrovascular ischemic events, Lancet, 338:1345-1349.

Townsend, Jun. 2007, Extended platelet storage makes a welcome difference, Medical Laboratory Observer, 39(6):40-41.

Tschoepe et al., 1993, Platelets in Diabetes: the role in Hemostatic Regulation in Atherosclerosis, Semin Thromb Hemost, 19(2):122-128.

Valeri et al., Jun. 2004, Effect of thrombopoietin alone and a combination of cytochalasin B and ethylene glycol bis(B-aminoethyl ether) N,N-tetraacetic acid-AM on the survival and function of autologous baboon platelets stored at 4° C for as long as 5 days, Transfusion, 44:865-870.

Van Aelst et al., 1997, Rho GTPases and signaling networks, Genes Dev, 11:2295-2322.

Voncken et al., Dec. 15, 1995, BCR/ABL P210 and P190 Cause Distinct Leukemia in Transgenic Mice, Blood, 86(12):4603-4611.

Voncken et al., Mar. 10, 1995, Increased Neutrophil Respiratory Burst in bcr-Null Mutants, Cell, 80:719-728.

Wang et al., 2006, Cell type-specific functions of Rho GTPases revealed by gene targeting in mice, Trends in Cell Biology, 17(2):58-64.

Waszkowycz et al., 2001, Large-scale virtual screening for discovering leads in the postgenomic era, IBM Systems J, 40:360-376.

Weber et al., 2011, Pathogen-Reduction for Platelet Concentrates, Clin. Lab., 57:293-295.

White, 1982, Influence of Taxol on the Response of Platelets to Chilling, Taxol, 108(2):184-195.

White, Aug. 1968, Effects of Colchicine and Vinca Alkaloids on Human Platelets, Platelet Contractility, 53(2): 281-291.

Winocour, 1992, Platelet Abnormalities in Diabetes Mellitus, Diabetes, 41(Suppl 2):26-31.

Winokur et al., Apr. 1, 1995, Mechanism of Shape Change in Chilled Human Platelets, Blood, 85(7):1796-1804.

Worthylake et al., 2000, Crystal structure of Rac1 in complex with the quinine nucleotide exchange region of Tiam1, Nature, 408:682-688.

Xu et al., Jun. 2013, Temperature cycling improves in vivo recovery of cold-stored human platelets in a mouse model of transfusion, Transfusion, 53:1178-1186.

Yang et al., 2007, Pho GTPase Cdc42 coordinates hematopoletic stem cell quiescence niche interaction in the bone marrow, PNAS, 104(12):5091-5096.

Zhao et al., May 2003, Human mammary epithelial cell transformation through the activation of phosphatidylinositol 3-kinase, Cancer Cell, 3(5):483-495.

Zheng et al., 1995, Direct Involvement of the Small GTP-binding Protein Rho in Ibc Oncogene Function, J Biol Chem, 270:9031-9034.

Zheng, 2001, Dbl family guanine nucleotide exchange factors, Trends Biochem Sci, 26:724-732.

Zhou et al., 2013, Cell Type-specific Signaling Function of RhoA GTPase: Lessons from Mouse Gene Targeting, The Journal of Biological Chemistry, 288(51):36179-36188.

International Search Report and Written Opinion dated Mar. 4, 2021 for application No. PCT/US2021/013311.

PLATELET STORAGE METHODS AND COMPOSITIONS

CROSS REFERENCE TO RELATED APPLICATIONS

This patent application is a U.S. National Phase Application of PCT International Application PCT/US2021/013311, filed Jan. 13, 2021, designating the United States of America and published in the English language, which is an International Application of and claims the benefit of priority to U.S. Provisional Application No. 62/961,580, filed Jan. 15, 2020. All of the foregoing applications are fully incorporated herein by reference in their entireties for all purposes.

GOVERNMENT SUPPORT CLAUSE

This invention was made with government support under HL123103, HL158688, HL119810, and HL147536 awarded by the National Institutes of Health. The government has certain rights in the invention.

STATEMENT REGARDING FEDERALLY SPONSORED R&D

This invention was made with government support under R01 HL147536, R43 HL123103, and UH54HL119810 awarded by the National Institutes of Health. The government has certain rights in the invention.

BACKGROUND

Field

The present application relates to the fields of chemistry, biology, and medicine. Disclosed herein are chemical compositions and their methods of use. More particularly, disclosed herein are compounds, compositions for platelet storage, methods of platelet storage and methods of using such stored platelets.

Description

Platelet transfusion is a common life-saving procedure to treat hemorrhage or to prevent bleeding in patients with low platelet counts or dysfunctional platelets, including cancer patients receiving chemotherapy. Recently, the application of large doses of platelets during resuscitation has been shown to significantly improve survival of trauma patients. Approximately 3 million doses of platelets are used in the USA alone each year. However, the current supply of platelets cannot effectively cope with the increased demand mainly because platelets, unlike other blood cells, can be stored only at room temperature but not in refrigeration.

Room temperature storage favors bacteria growth, and the risk of bacterial infection of platelet concentrate transfusion is estimated to be 50 times higher than that of refrigerated red blood cell products. Thus, the U.S. FDA limits platelet room temperature storage to up to 7 days, and actual shelf life is only 2.5-3 days with a growing list of FDA mandated tests for microbiological contamination after platelet collection from donors. Up to 20% of platelet products are discarded due to expiration. Yet there are constant platelet shortages due to unpredictable increased usage in surgery, chemotherapies, and trauma situations. Short shelf life represents a major handicap to converting platelet products into effective commodities, and an effective method to safely store human platelets for an extended period of time is a hugely unmet medical need globally, which has been extensively studied but still without a solution.

Refrigerated platelets (1-6° C.), while hemostatically active, are rapidly cleared from circulation after transfusion, and the mechanism of this clearance system has been a longstanding mystery. The U.S. CFR allows for the use of cold platelets for up to 3 days of storage for trauma patients (21 CFR 640.24 and 640.25).

The development of a method to prevent platelet damage upon refrigeration for longer periods of time is a much needed, and long sought advance in blood banking. Such development would revolutionize the current method of platelet storage.

SUMMARY

Some embodiments provide a compound having the structure of Formula (I)

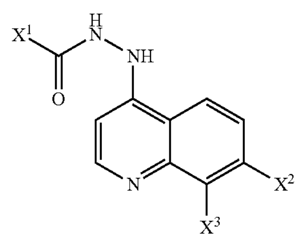

or a pharmaceutically acceptable salt thereof, wherein:

$X^1$ is an optionally substituted aryl or optionally substituted heteroaryl;

$X^2$ is selected from the group consisting of hydrogen, halogen, and optionally substituted alkyl; and $X^3$ is hydrogen or an optionally substituted alkyl.

In some embodiments, $X^1$ is an optionally substituted aryl. In some embodiments, $X^1$ is an optionally substituted heteroaryl. In some embodiments, $X^1$ is a substituted phenyl. In some embodiments, $X^1$ is a 3,4-dichlorophenyl or a 4-methylphenyl. In some embodiments. $X^1$ is an unsubstituted heteroaryl. In some embodiments, $X^1$ is an unsubstituted 2-indole. In some embodiments, $X^2$ is hydrogen. In some embodiments, $X^2$ is chloride. In some embodiments, $X^2$ is trifluoromethyl. In some embodiments, $X^3$ is hydrogen. In some embodiments, $X^3$ is trifluoromethyl.

In some embodiments, a compound of Formula (I) is selected from the group consisting of

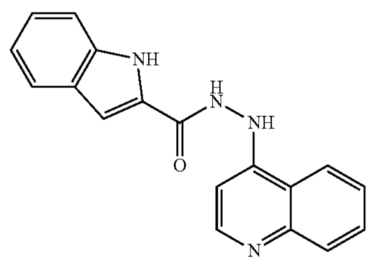

,

-continued

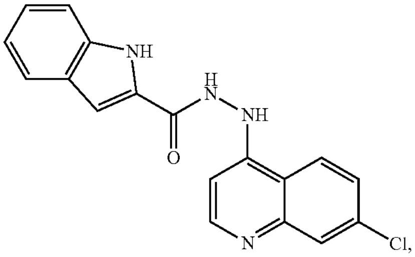

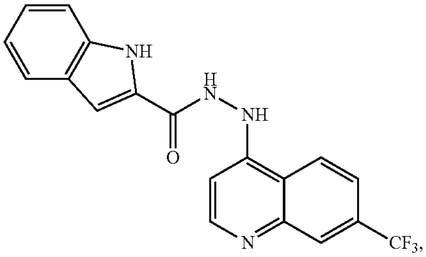

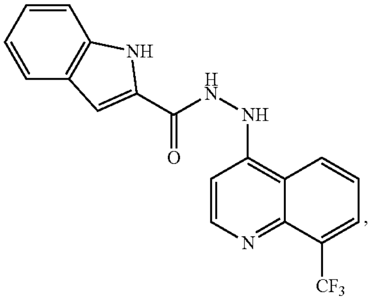

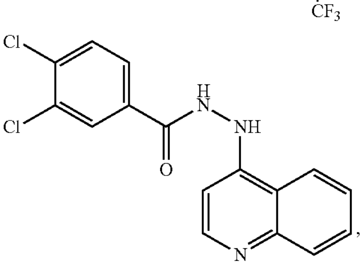

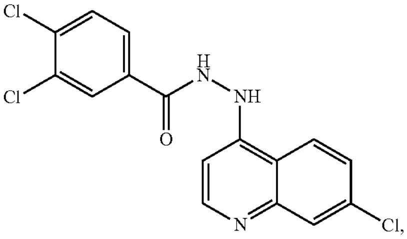

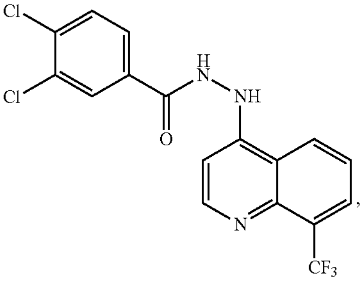

-continued

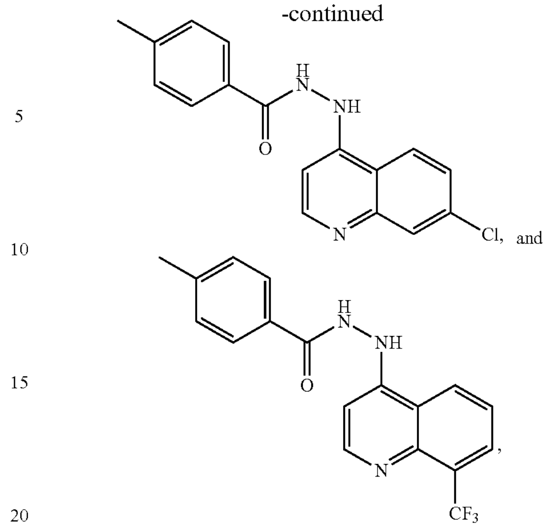

and or a pharmaceutically acceptable salt thereof.

Some embodiments relate to a composition for cold platelet storage at 0 to 20° C. In some embodiments, the composition comprises platelets, a compound of Formula (I) or pharmaceutically acceptable salt thereof, or combinations thereof, and a physiologically acceptable carrier, wherein said compound is present at a concentration of about 1 μM to about 20 μM. In some embodiments, the carrier is a buffer. In some embodiments, the carrier is selected from platelet additive solution (PAS), saline, phosphate buffered saline, Tris buffered saline, Hank's buffered saline, water, or a combination thereof. In some embodiments, the carrier comprises an electrolyte solution. In some embodiments, the composition comprises an additive selected from NaCl, KCl, CaCl2, $MgCl_2$, $MgSO_4$, $Na_3$ citrate, citric acid, $NaHCO_3$, Na phosphate, Na acetate, Na gluconate, glucose, maltose, mannitol, and combinations thereof. In some embodiments, the additive is present in an amount from about 0.5 mmol/L to about 150 mmol/L. In some embodiments, further comprises one or more ingredients selected from D-ribose, D-glucose, Hanks solution, Hepes solution, bovine serum albumin, tic anticoagulant peptide and sterile water, or combinations thereof. In some embodiments, the composition further comprises an additive selected from pH adjusting and buffering agents, tonicity adjusting agents, stabilizers, wetting agents, and combinations thereof. In some embodiments, the composition has a pH from about 5 to about 8. In some embodiments, the composition is isotonic.

Some embodiments relate to a method for storing platelets. In some embodiments, the method comprises storing said platelets in the presence of a compound of Formula (I) or a pharmaceutically acceptable salt thereof. In some embodiments, the method comprises storing platelets comprising storing the platelets in a composition as described herein. In some embodiments, the platelets are stored for a period of 10-14 days. In some embodiments, the storing is carried out at a temperature from about 0° C. to about 10° C. In some embodiments, the storing is carried out at a temperature from about 1° C. to about 6° C. In some embodiments, the storing is carried out at a temperature of about 2° C.

Some embodiments relate to a method for improving platelet survival upon transfusion. In some embodiments, the method comprises contacting platelets with a compound as described herein or a pharmaceutically acceptable salt thereof, or the composition as described herein, or the platelets stored according to a method as described herein, and infusing said contacted platelets into a subject. In some embodiments, the compound is present at a concentration from about 1 μM to about 20 μM. In some embodiments, the platelets are stored in the presence of the compound at a temperature of about 1° C. to about 25° C. In some embodiments, the platelets are stored in the presence of the compound for a period of about 1 to about 14 days. In some embodiments, the platelets are further contacted with a physiologically acceptable carrier.

DETAILED DESCRIPTION

In one aspect, a compound is provided having a structure of Formula (I)

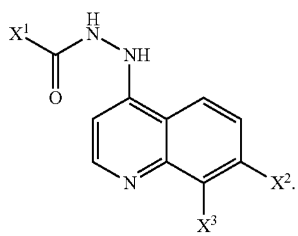

In some embodiments, Formula (I) may be in the form a pharmaceutically acceptable salt as described herein.

In some embodiments of the compounds of Formula (I), $X^1$ is selected from an optionally substituted aryl, an optionally substituted heteroaryl, a substituted phenyl, a 3,4-dichlorophenyl, a 4-methylphenyl, $X^1$ is an unsubstituted heteroaryl, or an unsubstituted 2-indole. In some embodiments of the compounds of Formula (I), $X^1$ is an optionally substituted aryl. In some embodiments of the compounds of Formula (I), $X^1$ is an optionally substituted heteroaryl. In some embodiments of the compounds of Formula (I), $X^1$ is a substituted phenyl, in some embodiments of the compounds of Formula (I), $X^1$ is a 3,4-dichlorophenyl or a 4-methylphenyl. In some embodiments of the compounds of Formula (I), $X^1$ is an unsubstituted heteroaryl. In some embodiments of the compounds of Formula (I), $X^1$ is an unsubstituted 2-indole.

In some embodiments of the compounds of Formula (I), $X^2$ is selected from hydrogen, deuterium, chloride, or trifluoromethyl. In some embodiments of the compounds of Formula (I), $X^2$ is hydrogen. In some embodiments of the compounds of Formula (I), $X^2$ is chloride. In some embodiments of the compounds of Formula (I), $X^2$ is trifluoromethyl.

In some embodiments of the compounds of Formula (I), $X^3$ is selected from hydrogen, deuterium, or trifluoromethyl. In some embodiments of the compounds of Formula (I), $X^3$ is hydrogen. In some embodiments of the compounds of Formula (I), $X^3$ is trifluoromethyl.

In some embodiments, the compounds of Formula (I) are selected from the group consisting of

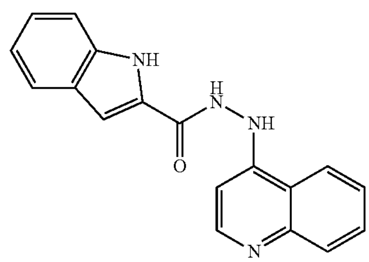

,

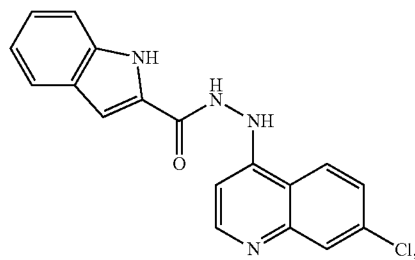

,

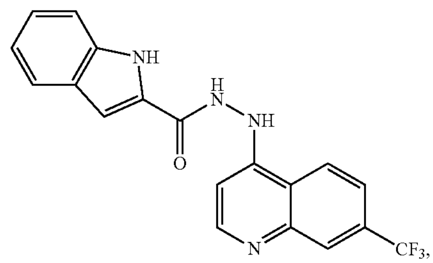

,

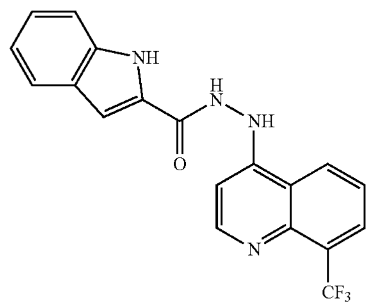

,

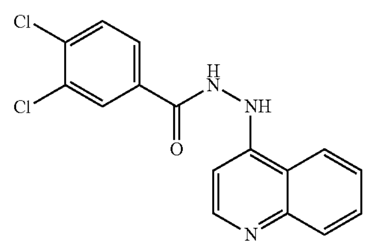

,

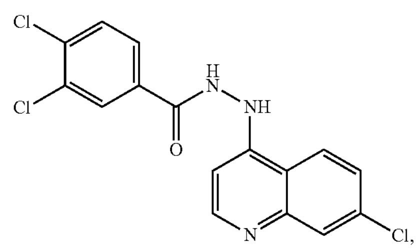

,

-continued

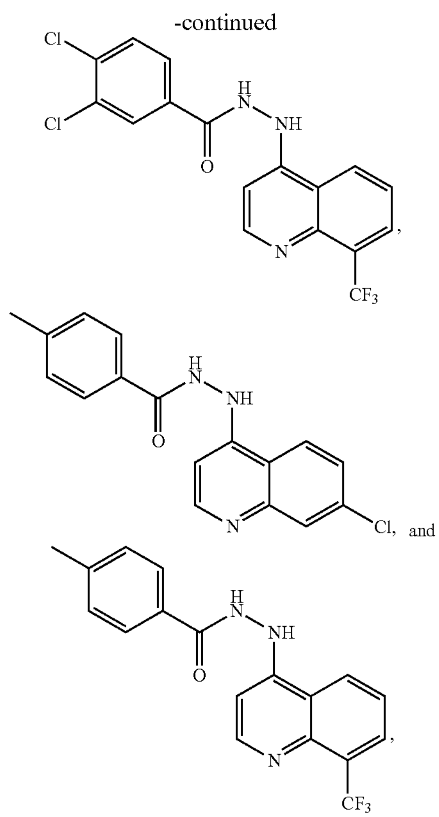

, and or a pharmaceutically acceptable salt thereof.

Some embodiments relate to a composition for cold platelet storage. In some embodiments, the composition comprises platelets and a compound of Formula (I) or a pharmaceutically acceptable thereof. In some embodiments, the composition comprises a combination of a compound of Formula (I) and a pharmaceutically acceptable thereof. In some embodiments, the composition further comprises a carrier.

In some embodiments, the storage is carried out at a temperature greater than 0° C., 2° C., 4° C., 6° C., 8° C., 10° C., 12° C., 14° C., 16° C., 18° C., 20° C., 22° C., 24° C., 26° C., 28° C. 30° C., or ranges including and/or spanning the aforementioned values. In some embodiments, the storage is carried out at a temperature from about 0° C. to about 25° C. In some embodiments, the storage is carried out at a temperature from about 0° C. to about 20° C. In some embodiments, the cold storage is carried out at a temperature from about 0° C. to about 10° C. In some embodiments, the cold storage is carried out at a temperature from about 1° C. to about 6° C. In some embodiments, the cold storage is carried out at a temperature of about 2° C.

In some embodiments, the carrier is a physiologically acceptable carrier. In some embodiments, said carrier is a buffer. In some embodiments, the carrier is selected from platelet additive solution (PAS), saline, phosphate buffered saline, Tris buffered saline, Hank's buffered saline, water, or a combination thereof. In some embodiments, carrier comprises an electrolyte solution. In some embodiments, the composition further comprises a pharmaceutically acceptable excipient. In some embodiments, the composition further comprises a stabilizer. Such materials should be non-toxic and should not interfere with the efficacy of the active ingredient. The pharmaceutically acceptable excipient, carrier, buffer, or stabilizer may take a wide variety of forms depending on the form of preparation desired for administration, e.g. intravenous or parenteral.

In some embodiments, the amount of the carrier (in mg) is equal to or greater than about: 0.1, 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or ranges including and/or spanning the aforementioned values. In some embodiments, the amount of the carrier present (in mg) is equal to or greater than about: 0.1, 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or ranges including and/or spanning the aforementioned values.

In some embodiments, the weight percent of carrier in the composition is equal to or greater than about: 0, 1, 2, 5, 10, 20, 30, 40, 50, 60, 70, 80. or ranges including and/or spanning the aforementioned values.

In some embodiments, the composition further comprises an additive. In some embodiments, the additive may be selected from pH adjusting and buffering agents, tonicity adjusting agents, stabilizers, wetting agents, and combinations thereof. In some embodiments, the additive may be selected from NaCl, KCl, $CaCl_2$, $MgCl_2$, $MgSO_4$, $Na_3$ citrate, citric acid, $NaHCO_3$, sodium phosphate, sodium acetate, sodium gluconate, glucose, maltose, mannitol, and combinations thereof. In some embodiments, the additive may be selected from D-ribose, D-glucose, Hanks solution, Hepes solution, bovine serum albumin, tic anticoagulant peptide and sterile water, or combinations thereof.

In some embodiments, the additive is present in an amount greater than 0.5 mmol/L, 1.00 mmol/L, 5 mmol/L, 10 mmol/L, 15 mmol/L, 20 mmol/L, 25 mmol/L, 30 mmol/L, 35 mmol/L, 40 mmol/L, 45 mmol/L, 50 mmol/L, 55 mmol/L, 60 mmol/L, 65 mmol/L, 70 mmol/L, 75 mmol/L, 80 mmol/L, 85 mmol/L, 90 mmol/L, 95 mmol/L, 100 mmol/L, 105 mmol/L, 110 mmol/L, 115 mmol/L, 120 mmol/L, 125 mmol/L, 130 mmol/L, 135 mmol/L, 140 mmol/L, 145 mmol/L, 150 mmol/L, 155 mmol/L, 160 mmol/L, 165 mmol/L, 170 mmol/L, 175 mmol/L, 180 mmol/L, 185 mmol/L, 190 mmol/L, 195 mmol/L, 200 mmol/L, or ranges including and/or spanning the aforementioned value. In some embodiments, the additive is present in an amount from about 0.5 mmol/L to about 150 mmol/L.

In some embodiments, the compound is present in an amount equal to or greater than: 0.1 μM, 1 μM, 2 μM, 3 μM, 4 μM, 5 μM, 6 μM, 7 μM, 8 μM, 9 μM, 10 μM, 12 μM, 14 μM, 15 μM, 16 μM, 18 μM, 20 μM, 22 μM, 24 μM, 25 μM, 26 μM, 28 μM, 30 μM, 32 μM, 34 μM, 35 μM, 36 μM, 38 μM, 40 μM, 42 μM, 44 μM, 45 μM, 46 μM, 48 μM, 50 μM, 52 μM, 54 μM, 55 μM, 56 μM, 58 μM, 60 μM, 62 μM, 64 μM, 65 μM, 66 μM, 68 μM, 70 μM, 72 μM, 74 μM, 75 μM, 76 μM, 78 μM, 80 μM, 82 μM, 84 μM, 85 μM, 86 μM, 88 90 μM, 92 μM, 94 μM, 95 μM, 96 μM, 98 μM, 100 μM, 105 μM, 110 μM, 115 μM, 125 μM, 130 μM, 140 μM, 150 μM, 160 μM, 170 μM, 180 μM, 190 μM, 200 μM, or ranges including and/or spanning the aforementioned values. Some embodiments, the compound is present in an amount of about 1 μM about 100 μM, Some embodiments, the compound is present in an amount of about 1 μM to about 70 μM, Some embodiments, the compound is present in an amount of about 1 μM to about 20 μM, Some embodiments, the compound is present in an amount of about 1 μM to about 10 μM, In some embodiments, the compound is present in an amount of about 1 μM to about 9 μM. In some embodiments, the compound is present in an amount of about 1 μM to about 5 μM. Some embodiments, the compound is present in an amount of about 5 μM to about 100 μM, Some embodiments, the compound is present in an amount of about 5 μM to about 70 μM, Some embodiments, the compound is present in an amount of about 5 μM to about 20 μM, Some embodiments, the compound is present in an amount of about 5 μM to about 10 μM, In some embodiments, the compound is present in an amount of about 5 μM to about 9 μM, Some embodiments, the compound is present in an amount of about 10 μM to about 100 μM, Some embodiments, the compound is present in an amount of about 10 μM to about 70 μM, Some embodiments, the compound is present in an amount of about 10 μM to about 20 μM.

in some embodiments, the composition has a pH from about 5, 5.5, 6.0, 6.5, 7.0, 7.5, 8, or ranges including and/or spanning the aforementioned values. In some embodiments, the composition is isotonic.

Some embodiments relate to a method for storing platelets. In some embodiments, the method comprises storing said platelets in the presence of a compound according to Formula (I). In some embodiments, the method comprises storing said platelets in any of the aforementioned compositions.

In some embodiments, the platelets are stored for a period of 1 day, 2 days, 3 days, 4 days, 5 days, 6 days, 7 days, 8 days, 9 days, 10 days, 11, days, 12 days, 13 days, 14 days, 15 days, 16 days, 17 days, 18 days, 19 days, 20 days, 21 days, or ranges including and/or spanning the aforementioned values. In some embodiments, the platelets are stored in the presence of the compound for a period of 1 day, 2 days, 3 days, 4 days, 5 days, 6 days, 7 days, 8 days, 9 days, 10 days, 11, days, 12 days, 13 days, 14 days, 15 days, 16 days, 17 days, 18 days, 19 days, 20 days, 21 days, or ranges including and/or spanning the aforementioned values. In some embodiments in some embodiments, the platelets are stored in the presence of the compound for a period of about 1 to about 14 days. In some embodiments, the platelets are stored in the presence of the compound for a period of about 10 to about 14 days.

In some embodiments, the platelets are stored in the presence of a compound of Formula (I) at a temperature greater than 0° C., 2° C., 4° C., 6° C., 8° C., 10° C., 12° C., 14° C., 16° C., 18° C., 20° C., 22° C., 24° C., 26° C., 28° C. 30° C., or ranges including and/or spanning the aforementioned values. In some embodiments, the platelets are stored in the presence of a compound of Formula (I) at a temperature from about 0° C. to about 25° C. In some embodiments, the platelets are stored in the presence of a compound of Formula (I) at a temperature from about 0° C. to about 20° C. In some embodiments, the platelets are stored in the presence of a compound of Formula (I) at a temperature from about 0° C. to about 10° C. In some embodiments, the platelets are stored in the presence of a compound of Formula (1) at a temperature about 1° C. to about 6° C. In some embodiments, the platelets are stored in the presence of a compound of Formula (1) at a temperature of about 2° C.

Some embodiments relate to a method for improving platelet survival upon transfusion. In some embodiments, the method comprises contacting platelets with a compound of Formula (I) or a pharmaceutically acceptable salt thereof, and infusing said contacted platelets into a subject.

in some embodiments, the compound is present in an amount equal to or greater than: 0.1 μM, 1 μM, 2 μM, 3 μM, 4 μM, 5 μM, 7 μM, 8 μM, 9 μM, 10 μM, 12 μM, 14 μM, 15 μM, 16 μM, 18 μM, 20 μM, 22 μM, 24 μM, 25 μM, 26 μM, 28 μM, 30 μM, 32 μM, 34 μM, 35 μM, 36 μM, 38 μM, 40 μM, 42 μM, 44 μM, 45 μM, 46 μM, 48 μM, 50 μM, 52 μM, 54 μM, 55 μM, 56 μM, 58 μM, 60 μM, 62 μM, 64 μM, 65 μM, 66 μM, 68 μM, 70 μM, 72 μM, 74 μM, 75 μM, 76 μM, 78 μM, 80 μM, 82 μM, 84 μM, 85 μM, 86 μM, 88 μM, 90 μM, 92 μM, 94 μM, 95 μM, 96 μM, 98 μM, 100 μM, 110 μM, 115 μM, 125 μM, 130 μM, 140 μM, 150 μM, 160 μM, 170 μM, 180 μM, 190 μM, 200 μM, or ranges including and/or spanning the aforementioned values. Some embodiments, the compound is present in an amount of about 1 μM to about 100 μM, Some embodiments, the compound is present in an amount of about 1 μM to about 70 μM, Some embodiments, the compound is present in an amount of about 1 μM to about 20 μM, Some embodiments, the compound is present in an amount of about 1 μM to about 10 μM, In some embodiments, the compound is present in an amount of about 1 μM to about 9 μM. In some embodiments, the compound is present in an amount of about 1 μM to about 5 μM. Some embodiments, the compound is present in an amount of about 5 μM to about 100 μM, Some embodiments, the compound is present in an amount of about 5 μM to about 70 μM, Some embodiments, the compound is present in an amount of about 5 μM to about 20 μM, Some embodiments, the compound is present in an amount of about 5 μM to about 10 μM, In some embodiments, the compound is present in an amount of about 5 μM to about 9 μM. Some embodiments, the compound is present in an amount of about 10 μM to about 100 μM, Some embodiments, the compound is present in an amount of about 10 μM to about 70 μM, Some embodiments, the compound is present in an amount of about 10 μM to about 20 μM.

In some embodiments, the platelets are stored in the presence of a compound of Formula (I) at a temperature greater than 0° C., 2° C., 4° C., 6° C., 8° C., 10° C., 12° C., 14° C., 16° C., 18° C. 20° C. 22° C. 24° C. 26° C. 28° C. 30° C., or ranges including and/or spanning the aforementioned values. In some embodiments, the platelets are stored in the presence of a compound of Formula (I) at a temperature from about 0° C. to about 25° C. In some embodiments, the platelets are stored in the presence of a compound of Formula (I) at a temperature from about 0° C. to about 20° C. In some embodiments, the platelets are stored in the presence of a compound of Formula (I) at a temperature from about 0° C. to about 10° C. In some embodiments, the platelets are stored in the presence of a compound of Formula (I) at a temperature about 1° C. to about 6° C. In some embodiments, the platelets are stored in the presence of a compound of Formula (I) at a temperature of about 2° C.

In some embodiments, the platelets are stored for a period of 1 day, 2 days, 3 days, 4 days, 5 days, 6 days, 7 days, 8 days, 9 days, 10 days, 11, days, 12 days, 13 days, 14 days, 15 days, 16 days, 17 days, 18 days, 19 days, 20 days, 21 days, or ranges including and/or spanning the aforementioned values. In some embodiments, the platelets are stored in the presence of the compound for a period of 1 day, 2 days, 3 days, 4 days, 5 days, 6 days, 7 days, 8 days, 9 days, 10 days, 11, days, 12 days, 13 days, 14 days, 15 days, 16 days, 17 days, 18 days, 19 days, 20 days, 21 days, or ranges including and/or spanning the aforementioned values. In some embodiments. In some embodiments, the platelets are stored in the presence of the compound for a period of about 1 to about 14 days. In some embodiments, the platelets are stored in the presence of the compound for a period of about 10 to about 14 days In some embodiments, the platelets are further contacted with a physiologically acceptable carrier.

Some embodiments relate to a composition comprising a compound of Formula (I) and a platelet additive solution (PAS), wherein each 100 mL of PAS comprises: Sodium chloride 0.405 g, Potassium chloride 0.037 g, Magnesium chloride $6H_2O$ 0.030 g, acetate $3H_2O$ 0.442 g, Sodium citrate $2H_2O$ 120 0.318 g, Sodium dihydrogen phosphate $1H_2O$ 0.093 g, Disodium phosphate $12H_2O$ 0.769 g, and water for injection s.p. 100 mL.

Unless defined otherwise, all technical and scientific terms used herein have the same meaning as commonly understood by one of ordinary skill in the art to which the embodiments belong. Although any methods and materials similar or equivalent to those described herein may also be used in the practice or testing of the embodiments, the preferred methods and materials are now described. All publications mentioned herein are expressly incorporated by reference in their entireties.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Definitions

As used herein and in the appended claims, the singular forms "a," "an," and "the" include plural referents unless the context clearly dictates otherwise. Thus, for example, reference to "a platelet" includes a plurality of such platelets and reference to "the carrier" includes reference to one or more carriers and equivalents thereof known to those skilled in the art, and so forth.

"Solvate" refers to the compound formed by the interaction of a solvent and a compound described herein, a metabolite, or salt thereof. Suitable solvates are pharmaceutically acceptable solvates including hydrates.

The term "pharmaceutically acceptable salt" refers to salts that retain the biological effectiveness and properties of a compound, which are not biologically or otherwise undesirable for use in a pharmaceutical. In many cases, the compounds herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group of the compounds may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group of the compounds may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an airs as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazotyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spire-connected fashion. Carbocyclyls may have any degree of saturation provided that at least one ring in a ring system is not aromatic. Thus, carbocyclyis include cycloalkyls, cycloalkenyls, and cycloalkynyls. The carhocyclyl group may have 3 to 20 carbon atoms, although the present definition also covers the occurrence of the term "carhocyclyl" where no numerical range is designated. The carhocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[1.4]nonanyl.

A "(carbocyclyl)alkyl" is a carbocyclyl group connected, as a substituent, via an alkylene group, such as "$C_{\cdot 4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatorn(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclypalkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-5}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—$SO_2$R" group in which R is selected from hydrogen. $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N($R_A$)$SO_2R_B$" group in which $R_A$ and $R_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N($R_A$)OC(=O)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—N($R_A$)OC(=S)$R_B$" group in which $R_A$ and $R_B$ are each independently selected from hydrogen, $C_{1-6}$ alkyl, $C_{2-6}$ alkenyl, $C_{2-6}$ alknyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{5-10}$ aryl, 5-10 membered heteroaryl, and 5-10 membered heterocyclyl, as defined herein.

An "N-amido" group refers to a "—N($R_A$)C(=O)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, carbocyclyl, $C_{6-10}$ aryl, 5-10 membered heteroaryl, and 5-10 membered heterocyclyl, as defined herein.

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkvnyl, $C_1$-$C_6$ heteroalkyl, haloalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), C3-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy (optionally substituted with halo, $C_1$-$C_6$ alkyl, $C_1$-$C_6$ alkoxy, $C_1$-$C_6$ haloalkyl, and $C_1$-$C_6$ haloalkoxy), sulthydryl (mercapto), halo($C_1$-$C_6$)alkyl (e.g., —$CF_3$), halo($C_1$-$C_6$)alkoxy (e.g., —$OCF_3$), $C_1$-C6 alkylthio, arylthio, amino, amino($C_1$-$C_6$)alkyl, nitro, O-carbamyl, N-carbamyl, O-thiocarbamyl, N-thiocarbainyl, C-amido, N-amido, S-sulfonamido, N-sulfonamido, C-carboxy, O-carboxy, acyl, cyanate, isocyanate, thiocyanato, isothiocyanato, sulfinyl, sulfonyl, and oxo (=O). Wherever a group is described as "optionally substituted" that group can be substituted with the above substituents.

In some embodiments, substituted group(s) is (are) substituted with one or more substituent(s) individually and independently selected from $C_1$-$C_4$ alkyl, amino, hydroxy, and halogen.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as $—CH_2—$, $—CH_2CH_2—$, $—CH_2CH(CH_3)CH_2—$, and the like. Other radical naming conventions clearly indicate that the radical is a di-radical such as "alkylene" or "alkenyiene."

Wherever a substituent is depicted as a di-radical (i.e. has two points of attachment to the rest of the molecule), it is to be understood that the substituent can be attached in any directional configuration unless otherwise indicated. Thus, for example, a substituent depicted as -AE- or

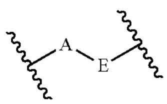

includes the substituent being oriented such that the A is attached at the leftmost attachment point of the molecule as well as the case in which A is attached at the rightmost attachment point of the molecule.

The term "platelet" is used here to refer to a blood platelet. A platelet can be described as a minisule protoplasmic disk occurring in vertebrate blood. Platelets play a role in blood clotting. The platelet may be derived from any source including a human blood supply, or the patient's own blood.

Where a range of values is provided, it is understood that the upper and lower limit, and each intervening value between the upper and lower limit of the range is encompassed within the embodiments.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviations, per the practice in the art. Alternatively, "about" can mean a range of up to 20%, up to 10%, up to 5%, and up to 1% of a given value. Alternatively, particularly with respect to biological systems or processes, the term can mean within an order of magnitude, within 5-fold, and within 2-fold, of a value. Where particular values are described in the application and claims, unless otherwise stated the term "about" meaning within an acceptable error range for the particular value should be assumed.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

It is understood that the methods and formulations described herein include the use of pharmaceutically acceptable salts and/or conformers of compounds of disclosed embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. Likewise, it is understood that the compounds described herein, include the compound in any of the forms described herein (e.g., pharmaceutically acceptable salts, enantiomeric forms, tautomeric forms, and the like).

The term "pharmaceutical composition" refers to a mixture of one or more compounds disclosed herein with other chemical components, such as diluents or carriers. The pharmaceutical composition facilitates administration of the compound to an organism. Pharmaceutical compositions will generally be tailored to the specific intended route of administration.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, C1-C7 alkylamine, cyclohexylamine, triethanolamine, ethylenediamine, and salts with amino acids such as arginine and lysine.

As used herein, a "carrier" refers to a compound that facilitates the delivery of a compound into cells or tissues. For example, without limitation, dimethyl sulfoxide (DMSO) is a commonly utilized carrier that facilitates the uptake of many organic compounds into cells or tissues of a subject.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

As used herein, the term "weight percent," when referring to a component, is the weight of the component divided by the weight of the composition that includes the component, multiplied by 100%. For example the weight percent of component A when 5 grams of component A is added to 95 grams of component B is 5% (e.g., 5 g A/(5 g A+95 g B)×100%).

The mechanisms of how cold temperatures affect platelet survival are not completely understood. The effects of cold temperature on platelets are believed to be complex and involve shape change, cytoskeletal reorganization, activation, cell surface protein clustering and changes in the carbohydrate structures of surface glycoproteins. Refrigerated storage is believed to reduce platelet life-span due to decreased temperature that cause glycoprotein-Ib (GPIb) receptors to cluster on specific niicrodomains of the platelet membrane. Applicant has found that recognition of specific glycated/syalylated residues on clustered glycoproteins by macrophage β2 integrins and hepatocyte Ashwell-Morell receptors results in platelet phagocytosis by the host and removal from circulation. Applicant postulates that changes in Rho GTPase activities may influence platelet membrane lipid raft assemby and glycoprotein composition. Reversible targeting of Rho family GTPases by small molecule inhibitors may prevent cytoskeleton-dependent refrigeration storage lesions in platelets and result in increased platelet survival.

Compositions and methods useful for platelet survival and/or quality, transfusion, and associated issues are disclosed herein. In one aspect, a composition for platelet storage or treatment is described.

The active agents described herein can form salts, which are also within the scope of the preferred embodiments. Reference to a compound of the active agent herein is understood to include reference to salts thereof, unless otherwise indicated.

EXAMPLES

Synthesis of UC-177633

UC-177633 was synthesized according to the following scheme.

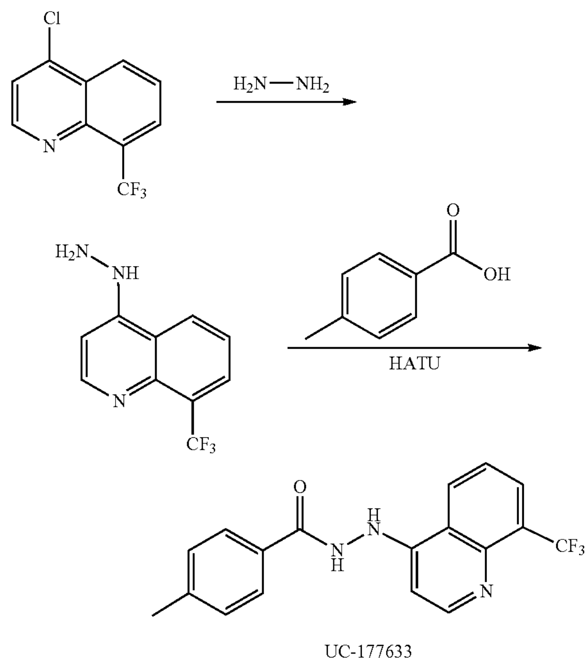

UC-177633

UC-177633 was synthesized in two steps:

Step 1: 4-chloro-8-(trifluoromethyl)quinolone was reacted with 2 equivalents of hydrazine in 5% mol PD[P(o-tolyl)3]2, CyPf-tBu, potassium hydroxine, dioxane at 100° C. for 8 hours to produce 4-hydrazineyl-8-(trifluoromethyl) quinoline.

Step 2: The resulting 4-hydrazineyl-8-(trifluoromethyl) quinolone was reacted with an equivalent amount of 4-methylbenzoic acid with 0.1 mmol HATU(1-[Bis(dimethylamino)methylene]-1H-1,2,3-triazolo[4,5-b]pyridinium 3-oxid hexafluorophosphate) with DMR at 0° C. for 1 hour and left overnight at room temerpature. The reaction mixture was diluted with ethyl acetate and the mixture was washed successively with 5% aqueous citric acid solution, saturated sodium bicarbonate solution and saturated sodium chloride solution. The organic layer was dried over anhydrous sodium sulphate, filtered and the solvent was removed in vacuo. The crude product was crystallized resulting in UC-177633.

The further compounds listed in Table 1 are synthesized following a similar sequence of steps, where the structural variations are provided by utilizing variants of the quinoline starting material or aromaticlheteroaromatic compound added at the coupling step. One of skill in the art will recognize that analogous synthesis schemes may be used to synthesize similar compounds. One of skill in the art will recognize that compounds of the present embodiments may be synthesized using other synthesis schemes.

Synthesis of UC-177617

UC-177617 was synthesized according to the following scheme.

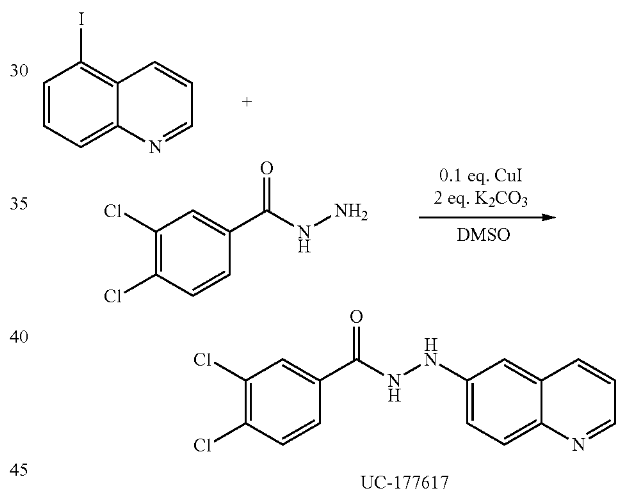

UC-177617

4-iodoquinoline was added to 1.5 equivalents of 3,4-dichlorobenzohydrazide. The reaction mixture underwent a CuI-catalyzed reaction with 0.1 equivalents of CuI, 0.2 equivalents potassium carbonate in DMSO at 60° C. for 20-30 hours. The resulting product yielded UC-177617 with an efficiency of about 70%.

The further compounds listed in Table 1 may be synthesized following a similar sequence of steps, where the structural variations. One of skill in the art will recognize that analogous synthesis schemes may be used to synthesize similar compounds. One of skill in the art will recognize that compounds of the present embodiments may be synthesized using other synthesis schemes.

Inhibition of Collagen-Induced Platelet Aggregation

Platelet shape change in washed platelets was monitored using an aggregometer and the decrease in light transmittance following addition of an agonist (Huzoor et al., 1993). For the purpose of this analysis, collagen was used as the agonist. Briefly, a washed human platelet suspension was incubated at 37° C. in a Lumi-Aggregometer (Chrono-Log Corporation) with stirring at 900 rpm, followed by the addition of dimethylsulfoxide (DMSO) as a control vehicle, or various compounds dissolved in DMSO. After incubating the samples with the respective compound for 2 minutes, platelet aggregation was induced by, adding collagen (1-4 μg/ml) and the relative aggregation value was read out at 6 min after the induction. A dose response for each compound was derived. These data were used to determine the $IC_{50}$ concentrations, at which 50% aggregation is reached. The results of these experiments are shown in Table 1.

TABLE 1

IC50 values for selected platelet aggregation inhibitors.

| Compound Number | Structure | $IC_{50}$ |
| --- | --- | --- |
| UC-177626 | 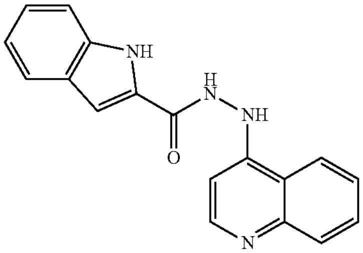 [SMILES: O=C(NNc1ccnc2ccccc12)c1cc2ccccc2[nH]1] | 10.1 μM |
| UC-177629 | 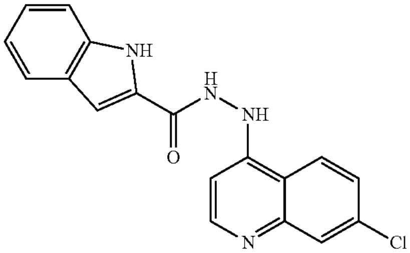 [SMILES: O=C(NNc1ccnc2cc(Cl)ccc12)c1cc2ccccc2[nH]1] | 2.3 μM |
| UC-177627 | 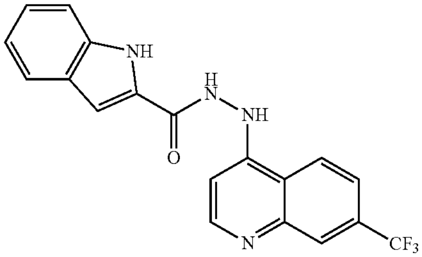 [SMILES: O=C(NNc1ccnc2cc(C(F)(F)F)ccc12)c1cc2ccccc2[nH]1] | 4.3 μM |
| UC-177628 | 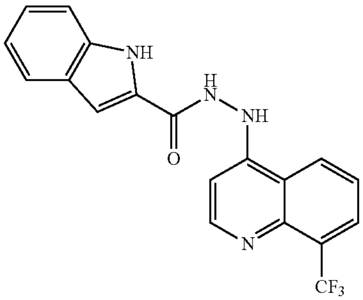 [SMILES: O=C(NNc1ccnc2c(C(F)(F)F)cccc12)c1cc2ccccc2[nH]1] | 5.8 μM |
| UC-177617 | 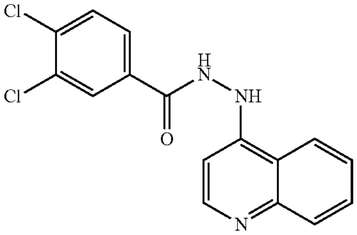 [SMILES: O=C(NNc1ccnc2ccccc12)c1ccc(Cl)c(Cl)c1] | 16.2 μM |

TABLE 1-continued

| IC50 values for selected platelet aggregation inhibitors. | | |
|---|---|---|
| Compound Number | Structure | $IC_{50}$ |
| UC-177619 | 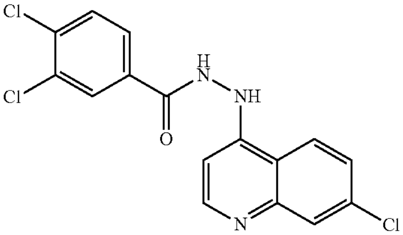 [SMILES: O=C(NNc1ccnc2cc(Cl)ccc12)c1ccc(Cl)c(Cl)c1] | 1.4 μM |
| UC-177618 | 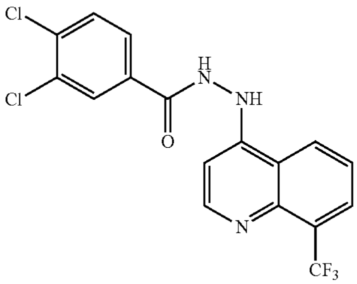 [SMILES: O=C(NNc1ccnc2c(C(F)(F)F)cccc12)c1ccc(Cl)c(Cl)c1] | 1.5 μM |
| UC-177634 | 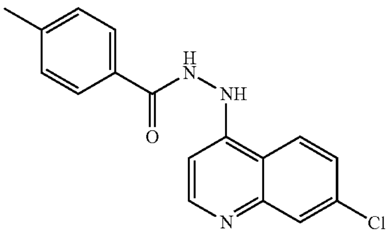 [SMILES: Cc1ccc(C(=O)NNc2ccnc3cc(Cl)ccc23)cc1] | 6.7 μM |
| UC-177633 | 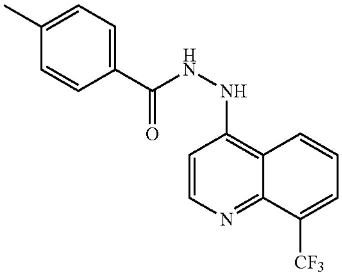 [SMILES: Cc1ccc(C(=O)NNc2ccnc3c(C(F)(F)F)cccc23)cc1] | 2.3 μM |

What is claimed is:

1. A compound of Formula (I):

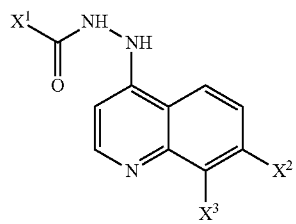

or a pharmaceutically acceptable salt thereof, wherein:

$X^1$ is selected from a 3,4-dichlorophenyl, a 4-methylphenyl, or an unsubstituted 2-indole;

$X^2$ is selected from the group consisting of hydrogen, deuterium, halogen, and optionally substituted alkyl; and $X^3$ is hydrogen, deuterium or an optionally substituted alkyl.

2. The compound of claim 1, wherein $X^1$ is a 3,4-dichlorophenyl or a 4-methylphenyl.

3. The compound of claim 1, wherein $X^1$ is an unsubstituted 2-indole.

4. The compound of claim 1, wherein $X^2$ is hydrogen or deuterium.

5. The compound of claim 1, wherein $X^2$ is chloro.

6. The compound of claim 1, wherein $X^2$ is trifluoromethyl.

7. The compound of claim 1, wherein $X^3$ is trifluoromethyl.

8. The compound of claim 1, selected from the group consisting of
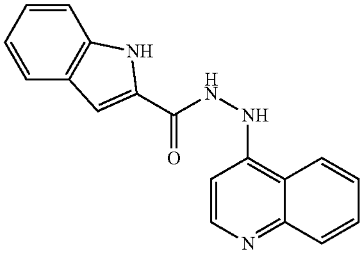
,
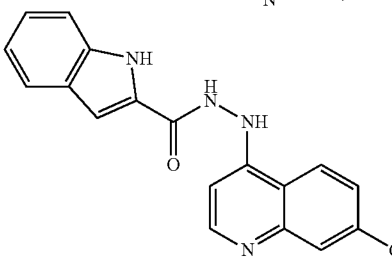
,
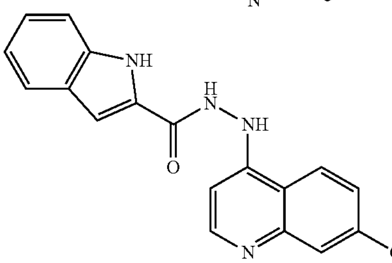
,
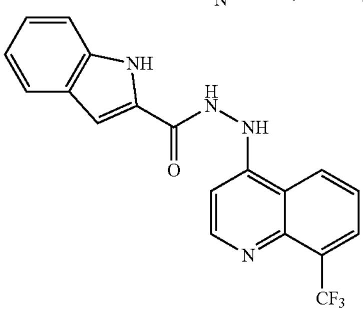
,
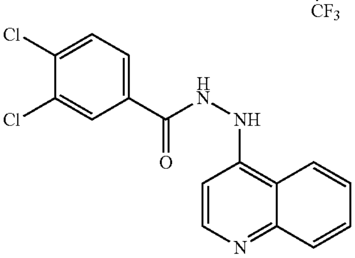
,
-continued
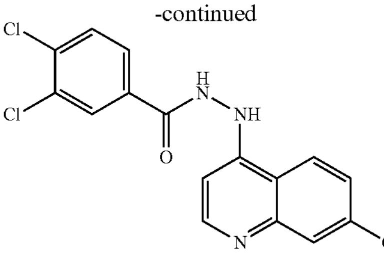
,
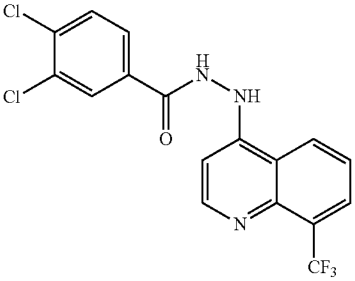
,
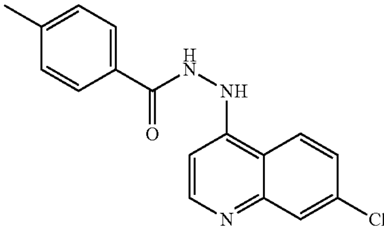
, and
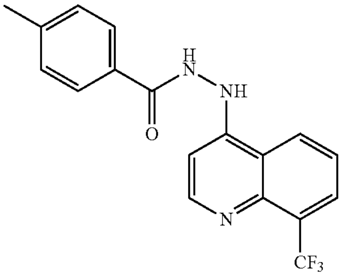
,
or a pharmaceutically acceptable salt thereof.
* * * * *